(12) United States Patent
Lee et al.

(10) Patent No.: US 8,748,579 B2
(45) Date of Patent: Jun. 10, 2014

(54) COLLAGEN-BASED MATRIX FOR USE AS RESTORATIVE MATERIAL, AND METHOD FOR PREPARING THE SAME

(75) Inventors: Seong-Ki Lee, Kyeonggi (KR); Si-Nae Park, Seoul (KR); Sang-Hee Bae, Kyeonggi (KR)

(73) Assignee: Dalim Tissen Inc., Seoul (KR)

( * ) Notice: Subject to any disclaimer, the term of this patent is extended or adjusted under 35 U.S.C. 154(b) by 703 days.

(21) Appl. No.: 12/423,972

(22) Filed: Apr. 15, 2009

(65) Prior Publication Data

US 2010/0040685 A1 Feb. 18, 2010

(30) Foreign Application Priority Data

Aug. 18, 2008 (KR) .......................... 10-2008-080360

(51) Int. Cl.
*C07K 1/00* (2006.01)
*A61K 38/17* (2006.01)

(52) U.S. Cl.
USPC ........................................ 530/356; 514/17.2

(58) Field of Classification Search
None
See application file for complete search history.

(56) References Cited

U.S. PATENT DOCUMENTS

| | | | |
|---|---|---|---|
| 5,350,583 A | | 9/1994 | Yoshizato et al. |
| 6,057,148 A | * | 5/2000 | Sugiyama et al. .......... 435/284.1 |
| 7,928,280 B2 | * | 4/2011 | Hariri et al. ..................... 602/48 |
| 2008/0033550 A1 | | 2/2008 | Taira |

FOREIGN PATENT DOCUMENTS

| | | |
|---|---|---|
| DE | 600 18 480 A1 | 2/2006 |
| DE | 600 18 480 T2 | 2/2006 |
| DE | 101 96 234 A1 | 4/2008 |
| DE | 101 96 234 B4 | 4/2008 |
| KR | 10-0520944 A1 | 10/2005 |
| KR | 10-0520944 B1 | 10/2005 |

OTHER PUBLICATIONS

Lee, Laminin Modified Infection-Preventing Collagen Membrane Containing Silver Sulfadiazine-Hyaluronan Microparticles, Artificial Organs, 26(6) 521-528, Blackwell publishing, 2002.*
Park, Si Nae, A Study of EDC-Crosslinked Collagen/Hyaluronic Matrix for Skin Tissue Replacement, Yonsei University, 2002, abstact, p. 1-127.*
Si-Nae Park, "A Study of EDC-crosslinked Collagen/Hyalurcnic Acid Matrix for Skin Tissue Replacement", Doctoral Thesis in Biomedical Engineering at Graduate School of Yonsei University, Published Jun. 2002, South Korea.

* cited by examiner

*Primary Examiner* — James H Alstrum Acevedo
*Assistant Examiner* — Jeannette Lieb
(74) *Attorney, Agent, or Firm* — Egbert Law Offices, PLLC

(57) ABSTRACT

Disclosed herein are a collagen-based matrix for use as a restorative material and a method for the preparation thereof. An atelocollagen dispersion is spread at a predetermined thickness over a plate and freeze-dried to form a porous collagen membrane. An atelocollagen dispersion is separately spread over a plate and pressurized to form a dense collagen membrane. This is overlaid with the porous collagen membrane and immersed in an EDS solution in ethanol to crosslink the two membranes with each other. From the bilayer structure thus constructed, EDS is removed, followed by lyophilization and cutting into an appropriate size.

8 Claims, 3 Drawing Sheets

COLLAGEN-BASED MATRIX FOR USE AS RESTORATIVE MATERIAL, AND METHOD FOR PREPARING THE SAME

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a collagen-based matrix for use as a restorative material. Particularly, the present invention relates to a collagen-based matrix with a bilayer structure composed of a dense layer and a porous layer, which is useful as a tissue restorative material offering excellent adhesiveness and healing effects. Type 1 collagen, typically obtained from animals, is converted into atelocollagen by removing telopeptides therefrom. The atelocollagen is dispersed in distilled water and forms a porous layer and a dense layer which are crosslinked with each other in the presence of EDC [1-ethyl-3-(3-dimethyl aminopropyl)carbodiimide] to afford a bilayer structure which is not separated in aqueous conditions and is processed into a matrix in a grid form. Thus, the present invention is also concerned with a method for preparing the collagen-based matrix.

2. Description of Related Art Including Information Disclosed Under 37 CFR 1.97 and 37 CFR 1.98

With the increase of a population of patients suffering from burns, bedsores, wounds, intractable ulcers, ulcerative dermal necrosis or epidermal necrosis, great advances have been made in the treatment of injured skin. Even three decades ago, patients with 60% or more of the body surface area burned usually died of septicemia. However, artificial skin has recently been developed to prevent water loss and bacterial infection, making a significant contribution to a reduction in mortality.

Artificial skin is largely divided into a wound dressing and a cultured skin. The former is typically applied to local or non-serious wounds to protect the skin before skin grafting is conducted thereat or until a cultured autograft is obtained, which takes usually 3 to 4 weeks. As for the cultured skin, it is used to minimize scarring when serious skin loss occurs or a wound is generated over a wide area of the skin. In this regard, sufficient dermal cells are obtained using cell culture technology and applied for permanent engraftment.

However, the cultured skin must be tested for safety from various pathogens including viruses (HIV 1&2, HTLV &, CMV lgM, Hepatitis B & C, and adenovirus) as well as that related to bacteria, fungi, endotoxins and mycoplasma. When obtained from a dead body, skin remains in an unknown health state, and it is impossible to perfectly sterilize it from the fatal viruses because the body tissue cannot be thermally treated to the desired extent. Further, it takes at least one week to culture and graft cells, which is too long to treat a first-aid patient therewith.

Over and above cultured skin, the wound dressing has advantages that it is used over a broad area of the skin, is easy to handle, and can be applied to first-aid patients. However, it is used only for temporary treatment, not for permanent engraftment. Wound dressings made of natural polymers, such as chitin, chitosan, collagen, etc. are low in mechanical strength, expensive and difficult to produce on a mass-scale. On the other hand, when prepared from synthetic polymers such as silicon or polyurethane, the wound dressings are poor in biocompatibility and in making contact with wounds.

BRIEF SUMMARY OF THE INVENTION

Accordingly, an object of the present invention is to overcome the problems encountered in the prior art and to provide a collagen-based matrix for use as a restorative material which is preventive of pathogen infection and which has an excellent mechanical strength.

Another object of the present invention is to provide a method of preparing a collagen-based matrix with a bilayer structure of a porous layer and a dense layer whereby the porous layer and the dense layer are crosslinked with each other to ensure a mechanical strength sufficient to stand up to and keep its integrity when in aqueous environments.

In accordance with an aspect, there is provided a method for preparing a collagen-based matrix, comprising: a first step of spreading a dispersion selected from among an atelocollagen dispersion (A), an infection-suppressive atelocollagen dispersion (B), a mixture dispersion of hyaluronic acid and atelocollagen (C) and a mixture dispersion of infection-suppressive atelocollagen and hyaluronic acid (D) for a porous layer over a Petri dish or a releasable plate to form a uniform membrane 0.05~1 mm thick, followed by lyophilization at −60~80° C. for 1~2 days to give a porous membrane; a second step of spreading an atelocollagen dispersion (E) for a dense layer over a releasable plate and applying a pressure of 1~20 psi to the spread dispersion to form a 0.05~1 mm thick, dense membrane; a third step of drying the dense membrane at room temperature for 10~20 min, overlaying the porous membrane on the dense membrane, and air-drying the membranes at room temperature for 1~2 days to afford a bilayer structure; a fourth step of stirring a 10~100 mM solution of EDC in 90~99 wt % ethanol at 4° C. for 10~15 min; a fifth step of completely immersing the bilayer structure in the EDC solution at 4° C. for 1~2 days to crosslink the porous membrane with the dense membrane; a sixth step of washing the bilayer structure 4~6 times with distilled water to remove EDC therefrom; a seventh step of lyophilizing the washed bilayer structure at −60~−80° C. for 1~2 days; and an eighth step of cutting the lyophilized bilayer structure to dimensions of from 200 μm×200 μm×200 μm to 10 mm×15 mm×15 mm.

Also provided is the collagen-based matrix prepared using the method.

BRIEF DESCRIPTION OF THE SEVERAL VIEWS OF THE DRAWINGS

The above and other objects, features and advantages of the present invention will be more clearly understood from the following detailed description taken in conjunction with the accompanying drawings.

DETAILED DESCRIPTION OF THE INVENTION

Figure 1:
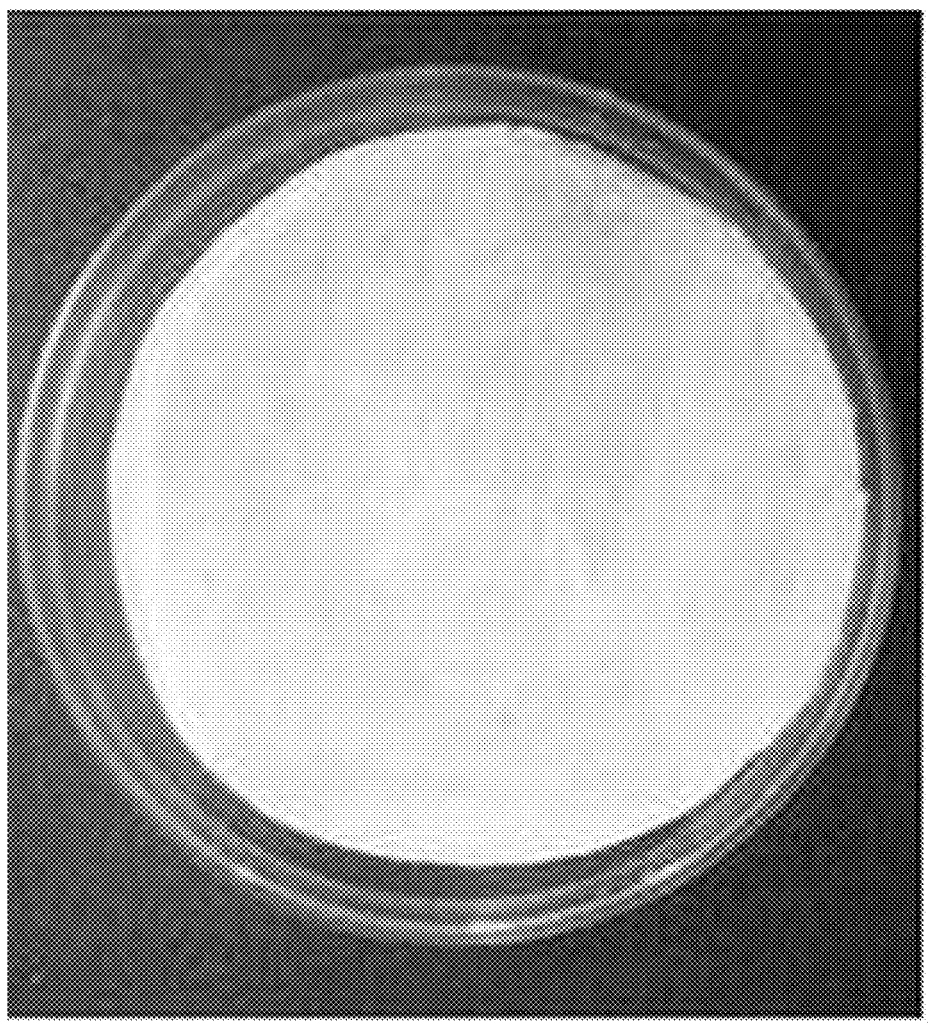
FIG. 1 shows a schematic view of a collagen-based matrix with a bilayer structure.
Figure 2:
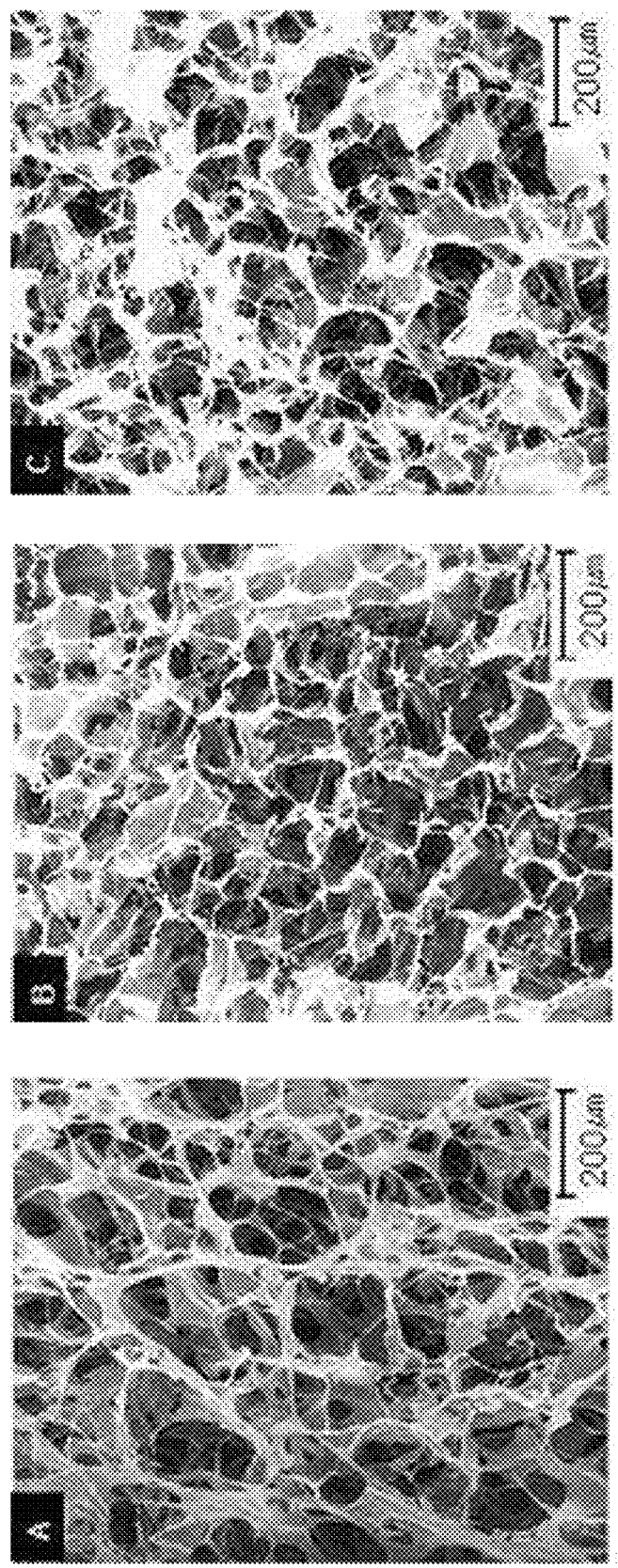
FIG. 2 shows electronic photographs of collagen-based matrixes with antibiotics incorporated therein: A: tobramycin, B: ciprofroxacin, C: polymixin B.
Figure 3:
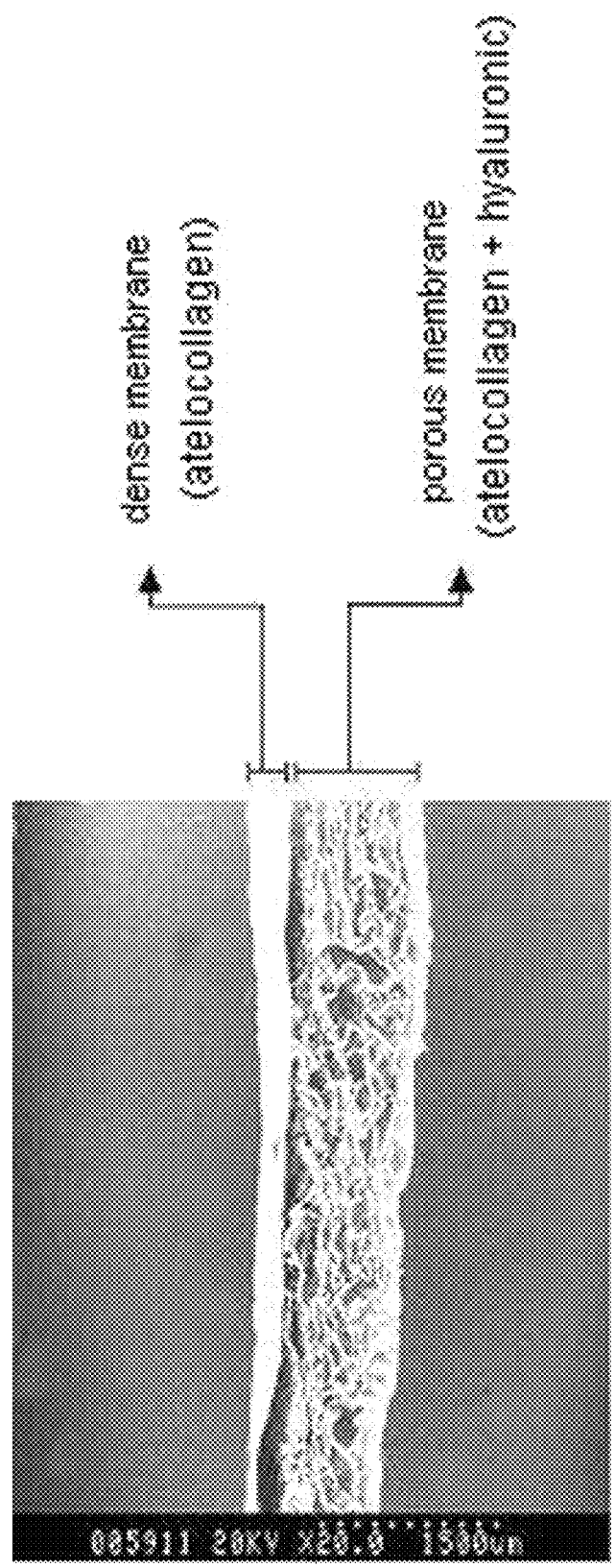
FIG. 3 shows a cross sectional view of the bilayer structure of the collagen-based matrix.

In contrast to conventional collagen-based matrixes using synthetic polymers in combination with natural polymers, the collagen-based matrix according to the present invention is composed only of the natural polymer collagen and thus is more compatible with bio-tissues.

In the collagen-based matrix, the bilayer structure constructed by crosslinking two component layers by use of EDC [1-ethyl-3-(3-dimethyl aminopropyl)carbodiimide] ensures strong mechanical strength and that it will keep its integrity in aqueous environments, thanks in addition to the use of 90~99% alcohol (ethyl alcohol, methyl alcohol) upon performing the crosslinking. Accordingly, the bilayer structure can be processed into a matrix with a dimension ranging from 200 μm×200 μm×200 μm to 10 mm×15 mm×15 mm, which can be tightly applied to even a narrow, curved region, such as irregular margins of a wound, the back of the hand, the face, the foot, etc., with the preservation of a moist condition therein. In addition, the collagen-based matrix of the present invention is readily used at any time, allowing for an treatment of a first-aid patient therewith.

Porcine collagen is preferred to bovine collagen in terms of safety from TSE's (Transmissible Spongiform Encephalopathies) infection. The addition of an antibiotic to the matrix greatly reduces the danger of secondary infection. In association with collagen fibers, further, hyaluronic acid, widely used in the tissue engineering and DDS (drug delivery system) fields, promotes cell migration.

In accordance with an aspect thereof, the present invention provides a method for preparing a collagen-based matrix for use as a restorative material. A detailed description will be given of the method, below.

The collagen-based matrix according to the present invention has a bilayer structure consisting of a porous layer and a dense layer, which are both obtained from atelocollagen dispersions. For the porous layer, an atelocollagen dispersion in distilled water (A), an infection-suppressive atelocollagen dispersion (B) obtained by adding an antibiotic to the dispersion (A), a mixture dispersion of atelocollagen and hyaluronic acid (C) in which hyaluronic acid is associated with collagen to reinforce the structure of collagen and improve cell migration, or an infection-suppressive mixture dispersion of collagen and hyaluronic acid (D) in which an antibiotic is added to the dispersion (C) is provided. A collagen dispersion (E) with a high content of collagen is also provided for generating a dense membrane.

For use in the formation of the porous layer and the dense layer, collagen dispersions are described, below.

1. Preparation of Atelocollagen Dispersion
1) Preparation of Atelocollagen Dispersions for Porous Layer
  (1) Collagen Dispersion for the Porous Layer (A)
  Atelocollagen is added in an amount of 1~3 wt % to distilled water and stirred at 4° C. for 1~2 days to give a dispersion, followed by adjusting the pH of the dispersion to 7.4 with 0.05~1 N NaOH.

(2) Infection-Suppressive Atelocollagen Dispersion (B)
  An antibiotic is added in a trace amount to the atelocollagen dispersion (A) to give an infection-suppressive atelocollagen dispersion.

(3) Mixture Dispersion of Atelocollagen and Hyaluronic Acid (C)
  Atelocollagen is added in an amount of 0.5~3 wt % to distilled water and stirred at 4° C. for 1~2 days to give an atelocollagen dispersion. Separately, hyaluronic acid is added in an amount of 1~3 wt % in distilled water and stirred at 4° C. for 13~24 hours. The atelocollagen dispersion is mixed with the hyaluronic acid solution at a weight ratio of 5~10: 0.5~2, followed by stirring at 4° C. and 8,000~10,000 RPM for 3~6 min. The pH of the resulting homogeneous mixture is adjusted to 7.4 with 0.05~1 N NaOH.

(4) Mixture Dispersion of Infection-Suppressive Atelocollagen and Hyaluronic Acid (D)
  A trace amount of an acid-insoluble antibiotic is homogeneously dispersed in the mixture dispersion (C) to give a mixture dispersion of infection-suppressive atelocollagen and hyaluronic acid.

2) Preparation of Atelocollagen Dispersion for the Dense Layer (E)
Atelocollagen is added in an amount of 2~5 wt % to distilled water and stirred at 4° C. for 1~2 days to give a dispersion, followed by adjusting the pH of the dispersion to 7.4 with 0.05~1 N NaOH.

2. Preparation of Collagen-Based Matrix as Restorative Material

A collagen-based matrix is prepared from the atelocollagen dispersion (A) or the infection-suppressive atelocollagen dispersion (B) for the porous layer and the atelocollagen dispersion (E) for the dense layer as follows.

A first step is spreading the atelocollagen dispersion (A) or the infection-suppressive collagen dispersion (B) over a Petri dish or a releasable plate to form a uniform membrane 0.05~1 mm thick, followed by lyophilization at −60~−80° C. for 1~2 days to give a porous membrane.

A second step is spreading the atelocollagen dispersion (E) over a releasable plate and applying a pressure of 1~20 psi to the spread dispersion to form a 0.05~1 mm thick, dense membrane.

A third step is drying the dense membrane at room temperature for 10~20 min, overlaying the porous membrane on the dense membrane, and air-drying the membranes at room temperature for 1~2 days to afford a bilayer structure.

A fourth step is stirring a 10~100 mM solution of EDC in 90~99 wt % ethanol at 4° C. for 10~15 min.

A fifth step is completely immersing the bilayer structure in the EDC solution at 4° C. for 1~2 days to crosslink the porous membrane with the dense membrane.

A sixth step is washing the bilayer structure 4~6 times with distilled water to remove EDC therefrom.

A seventh step is lyophilizing the washed bilayer structure at −60~−80° C. for 1~2 days.

An eighth step of cutting the lyophilized bilayer structure to a dimension of from 200 μm×200 μm×200 μm to 10 mm×15 mm×15 mm.

Alternatively, a collagen-based matrix may be prepared from a mixture dispersion of hyaluronic acid and atelocollagen (C) or a mixture dispersion of infection-suppressive atelocollagen and hyaluronic acid (D) for the porous layer and an atelocollagen dispersion (E) for the dense layer as follows. When collagen, extensively used in tissue engineering and DDSs (drug delivery systems), is associated therewith, the mucopolysaccharide hyaluronic acid can aid the migration of cells.

A first step is spreading the mixture dispersion of hyaluronic acid and atelocollagen (C) or the mixture dispersion of infection-suppressive atelocollagen and hyaluronic acid (D) over a releasable plate to form a uniform membrane 0.05~1 mm thick, followed by lyophilization at −60~−80° C. for 1~2 days to give a porous membrane.

A second step is spreading the atelocollagen dispersion (E) over a releasable plate and applying a pressure of 1~20 psi to the spread dispersion to form a 0.05~1 mm thick, dense membrane.

A third step is drying the dense membrane at room temperature for 10~20 min, overlaying the porous membrane on the dense membrane, and air-drying the membranes at room temperature for 1~2 days to afford a bilayer structure.

A fourth step is stirring a 10~100 mM solution of EDC in 90~99 wt % ethanol at 4° C. for 10~15 min.

A fifth step is completely immersing the bilayer structure in the EDC solution at 4° C. for 1~2 days to crosslink the porous membrane with the dense membrane.

A sixth step is washing the bilayer structure 4~6 times with distilled water to remove EDC therefrom.

A seventh step is lyophilizing the washed bilayer structure at −60~−80° C. for 1~2 days.

An eighth step is cutting the lyophilized bilayer structure to dimensions of from 200 μm×200 μm×200 μm to 10 mm×15 mm×15 mm.

A better understanding of the present invention may be realized through the following examples, which are set forth to illustrate, but are not to be construed to limit the present invention.

EXAMPLE 1

Preparation of Atelocollagen Dispersion (A) for the Porous Layer

Atelocollagen was added in an amount of 2 wt % to distilled water and stirred at 4° C. for 40 hours to give a dispersion, followed by adjusting the pH of the dispersion to 7.4 with 0.5 N NaOH.

Infection-Suppressive Atelocollagen Dispersion (B)

Penicillin V was added in a trace amount to the atelocollagen dispersion (A) to give an infection-suppressive atelocollagen dispersion.

Preparation of Atelocollagen Dispersion for the Dense Layer (E)

Atelocollagen was added in an amount of 4 wt % to distilled water and stirred at 4° C. for 30 hours to give a dispersion, followed by adjusting the pH of the dispersion to 7.4 with 0.5 N NaOH.

Preparation of Collagen-Based Matrix for Use as Restorative Material from Atelocollagen Dispersion (A) or Infection-Suppressive Atelocollagen Dispersion (B) for the Porous Membrane and Atelocollagen Dispersion (E) for the dense Membrane 1. The atelocollagen dispersion (A) was spread over a releasable plate to form a uniform, 0.5 mm thick, membrane, followed by lyophilization at −70° C. for 30 hours to give a porous membrane.

2. The atelocollagen dispersion (E) was spread over a releasable plate and pressurized under a pressure of 10 psi to form a 0.5 mm thick, dense membrane.

3. The dense membrane was dried at room temperature for 15 min, overlaid with the porous membrane, and air-dried at room temperature for 30 hours to afford a bilayer structure.

4. A 50 mM solution of EDC in 95 wt % ethanol was stirred at 4° C. for 15 min.

5. The bilayer structure was completely immersed in the EDC solution at 4° C. for 40 hours to crosslink the porous membrane with the dense membrane.

6. The bilayer structure was washed 5 times for 15 min with distilled water to remove EDC therefrom.

7. Then, the washed bilayer structure was lyophilized at −70° C. for 30 hours.

8. The lyophilized bilayer structure was cut to dimensions of from 200 μm×200 μm×200 μm to 10 mm×15 mm×15 mm.

EXAMPLE 2

An infection-suppressive atelocollagen-based matrix was prepared in a manner similar to that of Example 1, with the exception that the infection-suppressive atelocollagen dispersion (B) was used instead of the atelocollagen dispersion (A).

EXAMPLE 3

Preparation of Mixture Dispersion of Atelocollagen and Hyaluronic Acid (C)

Atelocollagen was added in an amount of 2 wt % to distilled water and stirred at 4° C. for 30 hours to give an atelocollagen dispersion. Hyaluronic acid was added in an amount of 2 wt % in distilled water and stirred at 4° C. for 20 hours to give a hyaluronic acid solution. The atelocollagen dispersion is mixed with the hyaluronic acid solution at a weight ratio of 7:1, followed by stirring at 4° C. and 9,000 rpm for 4 min. The pH of the resulting homogeneous mixture is adjusted to 7.4 with 0.5 N NaOH.

Preparation of Mixture Dispersion of Infection-Suppressive Atelocollagen and Hyaluronic Acid (D)

A trace amount of penicillin V is homogeneously dispersed in the mixture dispersion (C) to give a mixture dispersion of infection-suppressive atelocollagen and hyaluronic acid.

A collagen-based matrix was prepared from the atelocollagen dispersion from the mixture dispersion of atelocollagen and hyaluronic acid (C) or the infection-suppressive dispersion of atelocollagen and hyaluronic acid (D) for the porous layer and the atelocollagen dispersion (E) for the dense layer as follows.

1. The mixture dispersion of atelocollagen and hyaluronic acid (C) was spread over a releasable plate to form a uniformly 0.5 mm thick membrane, followed by lyophilization at −70° C. for 40 hours to give a porous membrane.

2. The atelocollagen dispersion (E) for the dense layer was spread over a releasable plate and pressurized under a pressure of 14 psi to form a 0.4 mm thick, dense membrane.

3. The dense membrane was dried at room temperature for 15 min, overlaid with the porous membrane, and air-dried at room temperature for 15 hours to afford a bilayer structure.

4. A 50 mM solution of EDC in 95 wt % ethanol was stirred at 4° C. for 15 min.

5. The bilayer structure was completely immersed in the EDC solution at 4° C. for 40 hours to crosslink the porous membrane with the dense membrane.

6. The bilayer structure was washed 5 times for 15 min with distilled water to remove EDC therefrom.

7. Then, the washed bilayer structure was lyophilized at −70° C. for 40 hours.

8. The lyophilized bilayer structure was cut to dimensions of from 200 μm×200 μm×200 μm to 10 mm×15 mm×15 mm.

EXAMPLE 4

An infection-suppressive atelocollagen-based matrix was prepared in a manner similar to that of Example 1, with the exception that the infection-suppressive dispersion of atelocollagen and hyaluronic acid (C) was used instead of the mixture dispersion of atelocollagen and hyaluronic acid (A).

Antibiotics useful in the present invention may include tetracyclines such as tetracycline, doxycycline and aureomycin, penicillins such as penicillin V, ampicillin, amoxicillin, bacampicillin, cabenicillin, carbenicillin, cloxacillin, dicloxacillin, nafcillin and oxacillin, cephalosprins such as cephalexin, cephradine, cefadroxil, cefaclor, cefuroxime axetil, cepfodoxime, loracarbef and cefixime, aminoglycosides such as gentamycin sulfate, tobramycin, amikacin, netimicin and neomycin, polymicins such as polymixin B, sulfoneamides such as mafenide, silver sulfadiazine and sulfasalazine, cell wall inhibitors such as teicoplanin, bacitracin and novobiocin, protein synthesis inhibitors such as clindamycin, and DNA synthesis inhibitors such as norfloxacin, enoxacin, pefloxacin, ciprofroxacin and ofloxacin, and may be used in a concentration of 0.001 mg~10 mg/ml.

When placed in a freeze-drier, the atelocollagen dispersion spread over a releasable plate is instantly frozen. In this condition, while drying is being conducted for a long period of time, fibrous dispersed particles aggregate together to form a sponge-like porous film. On the other hand, the atelocollagen dispersion spread over a releasable plate is pressurized using a dense porous absorbent plate such that the water leaches out and the fibrous collagen particles are brought into contact with each other to form a dense collagen membrane.

In addition to serving as a solvent for EDC and being used for crosslinking collagen membranes, the highly pure alcohol solution causes esterification with the carboxylic group (COOH) of collagen to impart on the collagen surface a cationic property which is apt to bind with negatively charged platelets.

When added to the atelocollagen, hyaluronic acid serves as a reinforcement for the weak structure of the porous membrane. Additionally, hyaluronic acid in association with collagen fibers improves cell migration, thus enhancing the healing effect.

As described hereinbefore, the collagen-based matrix according to the present invention is composed only of the natural polymer collagen and thus is more compatible with bio-tissues than are conventional collagen-based matrixes which employ synthetic polymers in combination with natural polymers. In the collagen-based matrix, the bilayer structure constructed by crosslinking two component layers by use of EDC [1-ethyl-3-(3-dimethyl aminopropyl)carbodiimide] ensures strong mechanical strength and keeps its integrity in aqueous environments thanks to the use of 90~99% alcohol (ethyl alcohol, methyl alcohol) when performing the crosslinking. Accordingly, the bilayer structure can be processed into a matrix with dimensions ranging from 200 µm×200 µm×200 µm to 10 mm×15 mm×15 mm, which can be tightly applied to cover even narrow, curved regions, such as the irregular margins of a wound, the back of a hand, the face, a foot, etc., with the preservation of a moist condition therein. In addition, the collagen-based matrix of the present invention is readily used at any time, allowing an emergent treatment of a first-aid patient therewith. Useful is Porcine collagen which is preferred to bovine collagen in terms of safety from TSE's. If necessary, an antibiotic is added to the matrix in order to greatly reduce the danger of secondary infection. In association with collagen fibers, further, hyaluronic acid, widely used in the tissue engineering and DDS (drug delivery system) fields, promotes cell migration.

Although the preferred embodiments of the present invention have been disclosed for illustrative purposes, those skilled in the art will appreciate that various modifications, additions and substitutions are possible. Accordingly, the modifications, additions and substitutions should be understood as falling within the scope and spirit of the invention.

We claim:

1. A method for preparing a collagen-based matrix, the method comprising:
    spreading a first atelocollagen dispersion or an infection-suppressive atelocollagen dispersion for a porous layer over a Petri dish or a releasable plate to form a uniform membrane followed by lyophilization to give a porous membrane;
    spreading a second atelocollagen dispersion for a dense layer over a releasable plate;
    applying an additional pressure of 1~20 p.s.i. directly to the spread dispersion by a dense porous absorbent plate in contact with the spread dispersion such that water leaches out and collagen particles are brought into contact with each other to form a dense membrane;
    partially drying the dense membrane at a room temperature for 10~20 minutes;
    overlaying the porous membrane on the partially dried dense membrane;
    completely air-drying the partially dried dense membrane together with the porous membrane to form a bilayer structure in which the porous membrane is bound to the dense membrane;
    immersing the bilayer structure in a solution containing a crosslinking agent to generate crosslinking between the porous membrane and the dense membrane in the bilayer structure;
    washing the bilayer structure to remove the crosslinking agent therefrom; and
    lyophilizing the washed bilayer structure.

2. The method according to claim 1, wherein the first atelocollagen dispersion is obtained by dispersing 1~3 wt % of atelocollagen in distilled water with stirring at 4° C. for 1~2 days and adjusting a pH of the solution to 7.4 with 0.05~1 N NaOH.

3. The method according to claim 1, wherein the second atelocollagen dispersion for the dense layer is obtained by dispersing 2~5 wt % of atelocollagen in distilled water with stirring at 4° C. for 1~2 days and adjusting a pH of the solution to 7.4 with 0.05~1 N NaOH.

4. The method according to claim 1, wherein the infection-suppressive atelocollagen dispersion is obtained by uniformly mixing an antibiotic in an amount of 0.001 mg~10 mg/ml in the first atelocollagen dispersion.

5. The method according to claim 4, wherein the antibiotic is selected from a group consisting of tetracyclines including tetracycline, doxycycline and aureomycin; penicillins including penicillin V, ampicillin, amoxicillin, bacampicillin, carbenicillin, cloxacillin, dicloxacillin, nafcillin and oxacillin; cephalosporins including cephalexin, cephradine, cefadroxil, cefaclor, cefuroxime, axetil, cepfodoxime, loracarbef and cefixime; aminoglycosides including gentamycin sulfate, tobramycin, amikacin, netimicin and neomycin; polymicins including polymixin B; sulfoneamides including mafenide, silver sulfadiazine and sulfasalazine; cell wall inhibitors including teicoplanin, bacitracin and novobiocin; protein synthesis inhibitors including clindamycin; and DNA synthesis inhibitors including norfloxacin, enoxacin, pefloxacin, ciprofroxacin and ofloxacin.

6. A method for preparing a collagen-based matrix, the method comprising:
    spreading a mixture dispersion of hyaluronic acid and atelocollagen or a mixture dispersion of infection-suppressive atelocollagen and hyaluronic acid over a releasable plate to form a uniform membrane followed by lyophilization to give a porous membrane;

spreading an atelocollagen dispersion over a releasable plate;

applying an additional pressure of 1~20 p.s.i. directly to the spread dispersion by a dense porous absorbent plate in contact with the spread dispersion such that water leaches out and collagen particles are brought into contact with each other to form a dense membrane;

partially drying the dense membrane at a room temperature for 10~20 minutes;

overlaying the porous membrane on the partially dried dense membrane;

completely air-drying the partially dried dense membrane together with the porous membrane to form a bilayer structure in which the porous membrane is bound to the dense membrane;

immersing the bilayer structure in a solution containing a crosslinking agent to generate crosslinking between the porous membrane and the dense membrane in the bilayer structure;

washing the bilayer structure to remove the crosslinking agent therefrom; and lyophilizing the washed bilayer structure.

7. The method according to claim 6, wherein the mixture dispersion of atelocollagen and hyaluronic acid is obtained by dispersing 0.5~3 wt % of atelocollagen in distilled water with stirring at 4° C. for 1~2 days to give an atelocollagen dispersion, dissolving 1~3 wt % of hyaluronic acid in distilled water with stirring at 4° C. for 13~24 hours to give a hyaluronic acid solution, mixing the atelocollagen dispersion with the hyaluronic acid solution at a weight ratio of 5~10:0.5~2, stirring the mixture at 4° C. and 8,000~10,000 r.p.m. for 3~6 minutes, and adjusting a pH of the resulting homogeneous mixture to 7.4 with 0.05~1 N NaOH.

8. The method according to claim 6, wherein the infection-suppressive mixture dispersion of atelocollagen and hyaluronic acid is obtained by adding an antibiotic in an amount of from 0.001 mg to 10 mg/ml to the mixture dispersion of atelocollagen and hyaluronic acid.

* * * * *